(12) United States Patent (10) Patent No.: US 8,319,183 B2
Gunasekaran et al. (45) Date of Patent: Nov. 27, 2012

(54) METHODS OF CHARACTERIZING AND MEASURING PARTICULATE FILTER ACCUMULATION

(75) Inventors: Natarajan Gunasekaran, Painted Post, NY (US); Vitor Marino Schneider, Painted Post, NY (US); Charlene Marie Smith, Corning, NY (US); Carlo Anthony Kosik Williams, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 695 days.

(21) Appl. No.: 12/582,981

(22) Filed: Oct. 21, 2009

(65) Prior Publication Data

US 2010/0108890 A1 May 6, 2010

Related U.S. Application Data

(60) Provisional application No. 61/110,185, filed on Oct. 31, 2008.

(51) Int. Cl.
*G01J 5/02* (2006.01)
(52) U.S. Cl. .................. 250/341.5; 250/340; 250/338.1; 324/637; 73/114.69; 73/114.71; 73/23.33
(58) Field of Classification Search ................. 250/341.5
See application file for complete search history.

(56) References Cited

U.S. PATENT DOCUMENTS

| | | | | |
|---|---|---|---|---|
| 4,477,771 A * | 10/1984 | Nagy et al. | ...................... | 324/636 |
| 5,157,340 A * | 10/1992 | Walton et al. | .................. | 324/641 |
| 5,497,099 A * | 3/1996 | Walton | ........................... | 324/641 |
| 5,500,599 A * | 3/1996 | Stange | ........................... | 324/634 |
| 5,710,430 A | 1/1998 | Nuss | | |
| 6,147,503 A * | 11/2000 | Nelson et al. | .................. | 324/637 |
| 7,157,919 B1 * | 1/2007 | Walton | ........................... | 324/641 |
| 7,357,822 B2 * | 4/2008 | Hamahata et al. | .............. | 55/283 |
| 7,679,374 B2 * | 3/2010 | Bromberg et al. | .............. | 324/637 |
| 8,210,033 B2 * | 7/2012 | Kondo et al. | .............. | 73/114.69 |
| 8,210,035 B2 * | 7/2012 | Imamura et al. | ........... | 73/114.75 |
| 2004/0200198 A1 * | 10/2004 | Inoue et al. | .................. | 55/282.3 |
| 2004/0232052 A1 * | 11/2004 | Call et al. | ....................... | 209/143 |
| 2006/0217612 A1 * | 9/2006 | Ouchi | .......................... | 600/407 |
| 2007/0209333 A1 * | 9/2007 | Kondou | ....................... | 55/282.3 |
| 2008/0059093 A1 * | 3/2008 | Bromberg et al. | .............. | 702/76 |
| 2008/0066621 A1 * | 3/2008 | Naito et al. | ....................... | 96/55 |
| 2008/0137068 A1 * | 6/2008 | Ouchi et al. | .................... | 356/51 |

* cited by examiner

*Primary Examiner* — David Porta
*Assistant Examiner* — Djura Malevic
(74) *Attorney, Agent, or Firm* — Walter M. Douglas (57) ABSTRACT

Methods of characterizing and measuring particulate accumulation in a family of particulate filters (10) are disclosed. The disclosure can be applied to diesel, gasoline and natural gas fueled engines, fluid streams bearing dust, and chemical and biological substances such as may be found in laboratory fluids, for example, air. In one embodiment, the disclosure is directed to measuring diesel particulate accumulation in a family of diesel particulate filters. The methods include measuring calibration complex terahertz transmission spectra ($P_C$ (f)) of at least a portion (17) of at least one particulate or diesel particulate filter in the family for different known particulate or diesel particulate amounts ($A_{DP}$). The method also involves performing a partial least squares (PLS) analysis on the calibration complex terahertz transmission spectra to establish a calibration relationship between the complex terahertz transmission spectra and the particulate or diesel particulate amounts. The complex transmission spectrum of a subject particulate filter or diesel particulate filter having an unknown amount of particulate or diesel particulate accumulation is then determined and compared to the linear calibration relationship to establish a measured amount of particulates or diesel particulates. The methods include using a terahertz (THz) system (100) to obtain the complex terahertz transmission spectra for the calibration and subject particulate or diesel particulate filters.

21 Claims, 6 Drawing Sheets

METHODS OF CHARACTERIZING AND MEASURING PARTICULATE FILTER ACCUMULATION

CROSS-REFERENCE TO RELATED APPLICATIONS

This application claims the benefit of priority under 35 U.S.C. §119(e) of U.S. Provisional Application Ser. No. 61/110,185 filed on Oct. 31, 2008.

FIELD

The present invention relates to particulate filters, and in particular, to methods of characterizing and measuring the accumulation of particulates in particulate filters, for example, particulate filters for diesel, gasoline and natural gas fueled engines, fluid streams bearing dust, and chemical and biological substances such as may be found in laboratory fluids such as air. The invention is further directed to a method for measuring selected properties of an article of manufacture.

BACKGROUND

Particulate filters (PFs) are designed to accumulate exhaust particulates ("soot") and are used in a variety of applications, including diesel and gasoline engined motor vehicles. PFs are ceramic-based structures that generally comprise a network of interconnected web walls that form a matrix of elongate, gas-conducting cells having a variety of cross-sectional shapes.

The performance of a PF depends in part on the amount of particulates it accumulates. A PF can be "regenerated" via thermal processing once the amount of accumulated particulates reaches a certain level. The success of the regeneration process, however, requires accurately determining the amount of accumulated particulates.

Present methods of determining particulate accumulation tend to be rather inaccurate because they rely on filter performance parameters a complex algorithm based on filter pressure drop values and engine operating parameters (time, speed, torque etc.). Often, the pressure drop values lead to either an under or over prediction of the amount of particulate matter accumulated in the DPF.

Knowing the precise amount of particulates in a particulate filter (for example, soot in a diesel particulate filter (a "DPF")) over a wide range of load levels allows for proper implementation of regeneration processes and increases filter durability. In addition, the efficiency of the current particulate or soot estimation methods would be significantly improved if low particulate or soot levels can be accurately measured.

What are needed therefore are methods for more accurately determining the amount of accumulated particulates for example soot in a PF.

SUMMARY

One aspect of the disclosure is a method of characterizing particulate accumulation in a family of PFs having a longitudinal axis and opposite first and second ends connected by an array of cells generally directed along the longitudinal axis. The method includes measuring calibration complex terahertz transmission spectra of at least a portion of at least one PF in the PF family and having different known particulate amounts. The method also includes performing a partial least squares analysis on the calibration complex terahertz transmission spectra, thereby establishing a linear calibration relationship between the calibration complex terahertz transmission spectra and the particulate amounts. The PFs can be selected from the group consisting of diesel, gasoline and natural gas fueled engines; fluid streams bearing dust or particulate matter, and chemical and biological substances such as may be found in laboratory fluids, for example, air.

Another aspect of the disclosure is a method of characterizing diesel particulate accumulation in a family of DPFs having a longitudinal axis and opposite first and second ends connected by an array of cells generally directed along the longitudinal axis. The method includes measuring calibration complex terahertz transmission spectra of at least a portion of at least one DPF in the DPF family and having different known diesel particulate amounts. The method also includes performing a partial least squares analysis on the calibration complex terahertz transmission spectra, thereby establishing a calibration relationship between the calibration complex terahertz transmission spectra and the diesel particulate amounts.

A further aspect of the disclosure is a method of measuring an amount of accumulated particulates in a subject PF, for example, a DPF, of a family of PFs. The method includes passing terahertz radiation through at least a portion of the array of cells from the first to the second end of the subject DPF to form transmitted terahertz radiation. The method also includes detecting the transmitted terahertz radiation and forming a subject complex terahertz transmission spectrum from the detected transmitted terahertz radiation. The method further includes comparing the subject complex terahertz transmission spectrum to a calibration relationship established by performing a partial least squares analysis on calibrated complex terahertz transmission spectra of at least one calibration PF in the PF family and having different known amounts of particulates.

Another aspect of the disclosure is a method of measuring an amount of accumulated diesel particulates in a subject DPF of a family of DPFs. The method includes passing terahertz radiation through at least a portion of the array of cells from the first to the second end of the subject DPF to form transmitted terahertz radiation. The method also includes detecting the transmitted terahertz radiation and forming a subject complex terahertz transmission spectrum from the detected transmitted terahertz radiation. The method further includes comparing the subject complex terahertz transmission spectrum to a linear calibration relationship established by performing a partial least squares analysis on calibrated complex terahertz transmission spectra of at least one calibration DPF in the DPF family and having different known amounts of diesel particulates.

Another aspect of the disclosure is a method of establishing a measured amount of diesel particulate accumulation in a subject PF of a family of PFs. The method includes measuring calibration complex terahertz transmission spectra of at least a portion of at least one PF in the PF family and having different known amounts of particulates, determined for example, by filter weight and volume. The method also includes performing a partial least squares analysis on the calibration complex terahertz transmission spectra, thereby establishing a calibration relationship between the calibration complex transmission spectra and amounts of particulates. The method also includes measuring a subject complex terahertz transmission spectrum for the subject PF and comparing the subject complex terahertz transmission spectrum to the calibration relationship to establish a measured amount of particulates in the subject PF.

Another aspect of the disclosure is a method of establishing a measured amount of diesel particulate accumulation in a subject DPF of a family of DPFs. The method includes measuring calibration complex terahertz transmission spectra of at least a portion of at least one DPF in the DPF family and having different known amounts of diesel particulates, determined for example, by filter weight and volume. The method also includes performing a partial least squares analysis on the calibration complex terahertz transmission spectra, thereby establishing a calibration relationship between the calibration complex transmission spectra and amounts of diesel particulates. The method also includes measuring a subject complex terahertz transmission spectrum for the subject DPF and comparing the subject complex terahertz transmission spectrum to the linear calibration relationship to establish a measured amount of diesel particulates in the subject DPF.

DETAILED DESCRIPTION

The term "particulate filter (PF)" as used herein means an filter for removing a solid material from a fluid stream is deemed to include, for example, "soot" from a diesel exhaust, particulates (solids) from the exhaust of gasoline and natural gas fueled engines as well as engines fueled by other hydrocarbon-based fuels, chemical and biological materials from air intake or venting systems provided such materials are sufficiently large that they cannot pass through the pores of the filter, and other fluid systems carrying solid materials (for example, dust in air streams from manufacturing processes). In addition, the term "particulate filter" is to be understood as an filter in which a particulate matter in fluid stream which passing through the filter can be purified with one part of the fluid stream passing through the walls of the filter to yield a fluid that is particulate-free fluid or substantially particulate-free and the other part (the "concentrate") passing though the channels of the filter with the particulate matter is concentrated therein Further, the term "soot" is a term of the art and specifically refers to the particulates accumulated in a PF or DPF. Herein, while diesel particulate filters ("DPFs") will be used to illustrate the disclosure, the techniques are applicable to other types of particulate filters (for example without limitation, gasoline or natural gas fired engines) and to measuring systems for articles to determine, without limitation, the content and/or type of selected fluids in the articles, web thickness, cracks and other characteristics.

Terahertz radiation excites the molecular structure and different molecular species or substances are excited at different terahertz spectral wavelengths. Terahertz frequencies (f) than can be used in practicing the invention are in the range of 0.05 THz to~15 THz (approximately 1.67-500 cm$^{-1}$). By knowing or determining the appropriate spectral wavelength for a given substance, one can determine the presence or absence of specific species and, by the use of standards or a calibration curve, can quantify the amount present. The process of the disclosure described herein, using a "DPF" as an example, can be used to determine particulates in other applications as mentioned herein and can be used to monitor manufacturing processes. For example, during the process of making ceramic honeycomb substrates such as are used in DPFs or pass-through catalytic converters a variety of solid materials are mixed together with the addition of water and, optionally, other fluids such as lubricants. Once the materials are thoroughly mixed (or "batched") the resulting "dough" is extruded to form a honeycomb extrudate called a "green body" which is then dried or partially dried so the green body does not slump. Afterward the dried green body is then "fired" to form a low thermal expansion honeycomb substrate that can be further process into the desired product. In order for the final product to perform according to specifications, it is important that its firing is properly carried out, and the amount of water remaining in the product can be used as a determinant of whether it was carried out. Using the method described herein, terahertz radiation can be passed side-to-side through the thickness of the honeycomb (that is, perpendicular to the channels of the honeycomb). Using standards or a calibration curve one can determine whether the firing was properly carried out. In addition, since the method using terahertz radiation can be used to determine whether there are internal cracks or voids in the honeycomb, and/or whether the walls of the honeycomb have a uniform thickness.

Reference is now made in detail to preferred embodiments of the disclosure, examples of which are illustrated in the accompanying drawings. Whenever possible, the same or like reference numbers and symbols are used throughout the drawings to refer to the same or like elements or components. While the following examples are directed to DPF's, the same principles as described in the following paragraphs would also be used in embodiments relating to particulates from the exhaust of gasoline and natural gas fueled engines as well as engines fueled by any other hydrocarbon-based fuel, chemical and biological materials from air intake or venting systems, and other fluid systems carrying solid materials (for example, dust in air streams from manufacturing processes).

Diesel Particulate Filters

Figure 1:
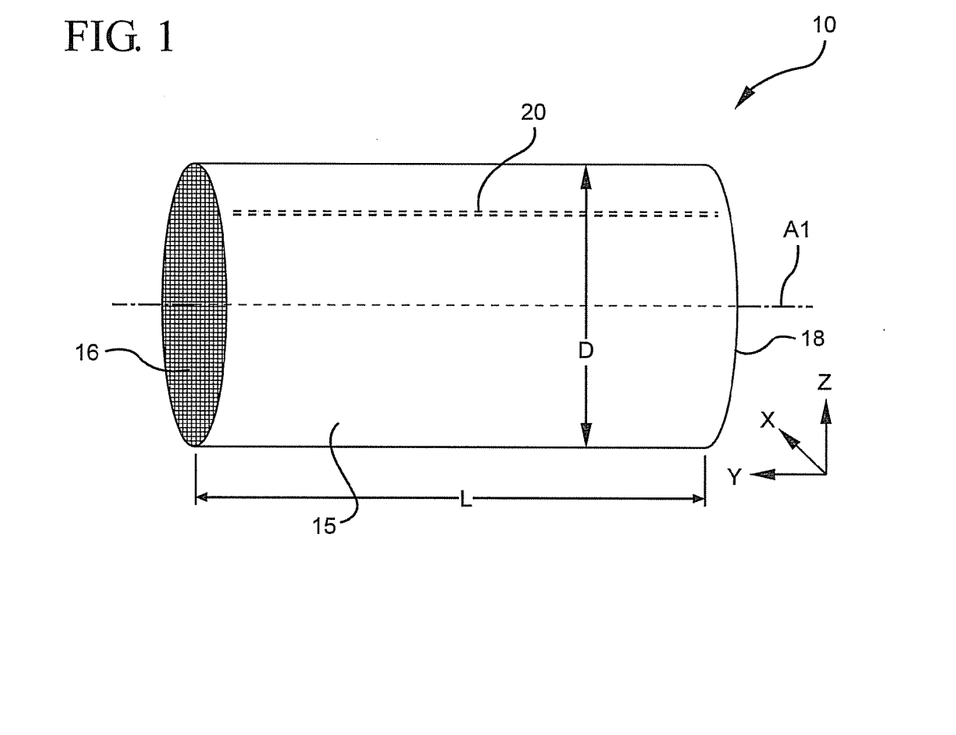
FIG. 1 is a perspective side view of an example DPF.
Figure 2:
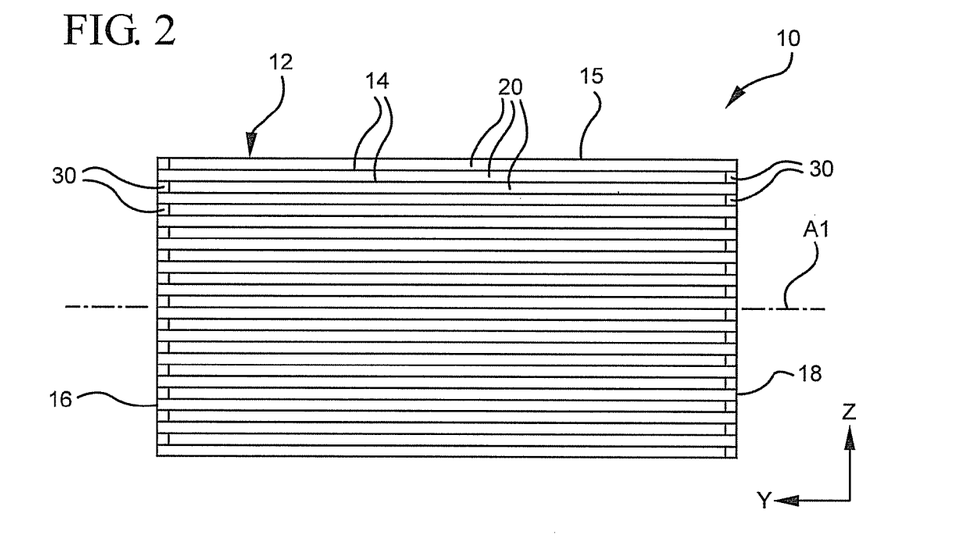
FIG. 2 is a cross-sectional view of a DPF similar to that shown in FIG. 1, showing the longitudinal cells and the alternating plugged cell ends.
Figure 3:
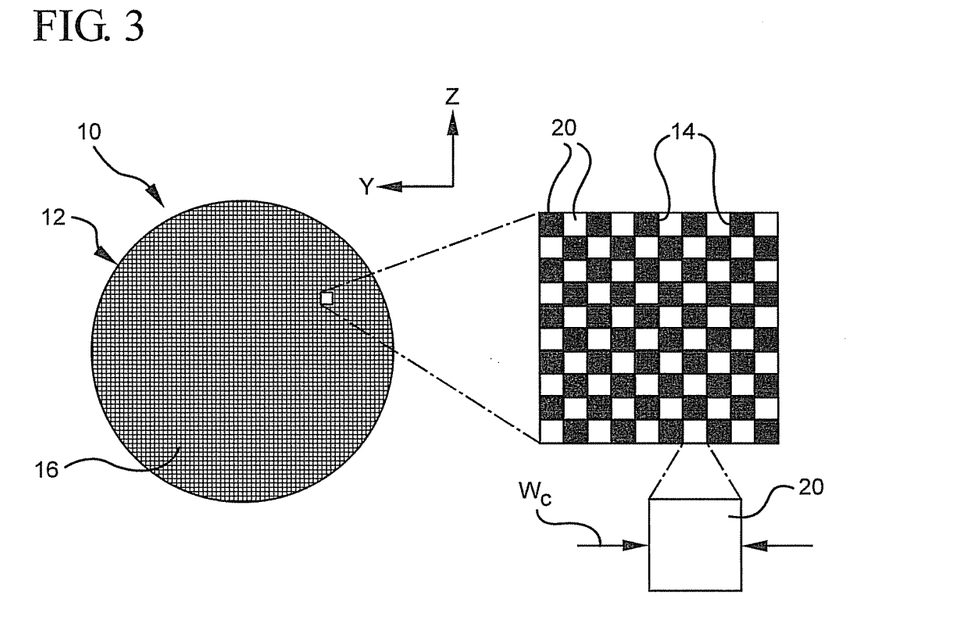
FIG. 3 is a close-up end view of the DPF of FIG. 1.

The present disclosure, in one embodiment, relates to diesel particulate filters (DPFs), and in particular relates to methods for characterizing and measuring the accumulation of diesel exhaust particulates in DPFs. FIG. 1 is a perspective side view of an example DPF 10. Cartesian coordinates are shown for the sake of reference. FIG. 2 is a cross-sectional view of DPF 10 similar to that of FIG. 1, and FIG. 3 is a close-up end view of the DPF of FIG. 1.

The typical DPF 10 has a honeycomb structure 12 with an axial length L, a diameter or width D and a central axis A1 that defines an axial (longitudinal) direction. Honeycomb structure 12 is formed by a matrix of intersecting, thin, porous walls 14 surrounded by an outer wall 15. Walls 14 extend across and between opposing ends 16 and 18, and form a large number of adjoining hollow channels or "cells" 20 that also extend between ends 16 and 18. Cells 20 are plugged with plugs 30 in an alternating fashion at ends 16 and 18 so that each cell has one open end and one plugged end. DPF 10 can have any type of cross-sectional shape, including square, rectangular, oval, circular, and the circular cross-sectional shape is shown by way of example.

An example DPF 10 has between about 100 and 400 cells per square inch and walls 14 that are generally on the order of 10-25 mils thick. The corresponding cell widths $W_C$ (FIG. 3) are typically in the range from about 8 mm to about 1.25 mm. Typical diameters D range from about 6 inches (about 15.24 cm) to about 15 inches (about 38.1 cm).

Example DPFs 10 are manufactured, for example, by extruding a plasticized ceramic-forming precursor of, for example, cordierite, mullite, silicon carbide, or aluminum titanate, through an extrusion die. The extruded "green body" is then cut and dried. Such green bodies are quite fragile and must be transported to a kiln, wherein the heat transforms the relatively soft and fragile green body into hardened, fired ware with rigid honeycomb structure 12, which is then plugged with plugs 30.

Figure 4:
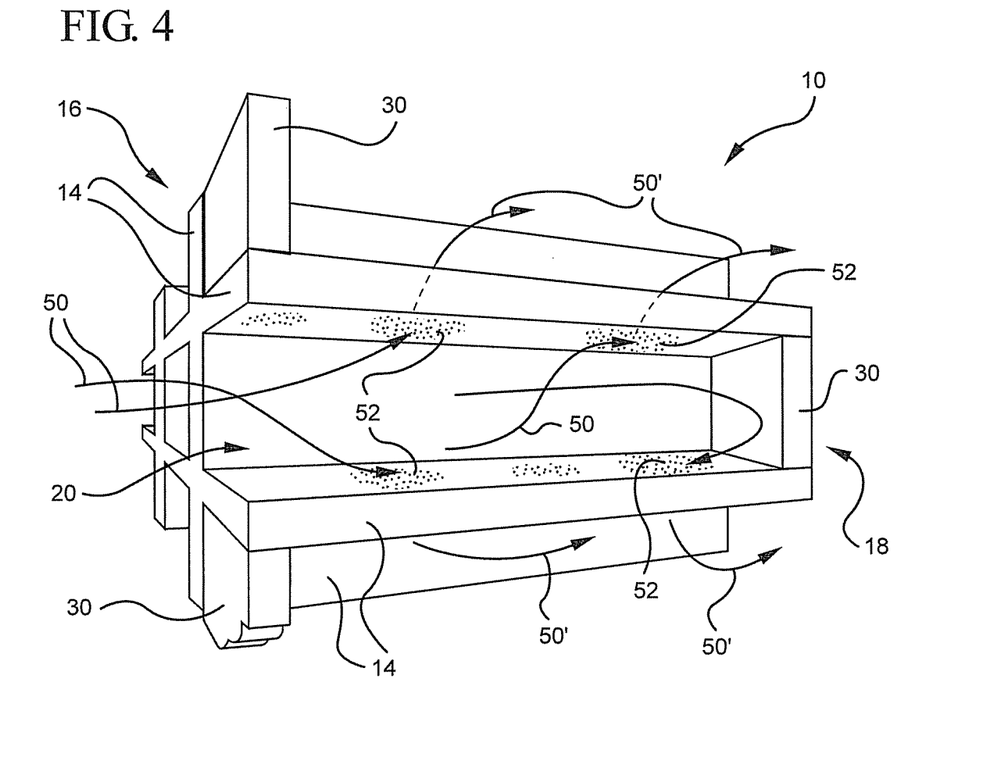
FIG. 4 is a close-up view of an end portion of a DPF and shows the flow of unfiltered diesel exhaust into the DPF and the flow of filtered diesel exhaust out of the DPF.

DPFs are used in diesel engines to filter diesel engine exhaust, which includes diesel particulates, also referred to in the art as "soot." FIG. 4 is a close-up view of an end portion of DPF 10 and shows the flow of unfiltered diesel exhaust 50 into end 16 of the DPF. Unfiltered diesel exhaust 50 contains diesel particulates 52. Because each cell 20 is blocked at one of its ends, the flow of diesel exhaust 50 into a given cell builds up pressure in a given cell, which causes the diesel exhaust to flow through porous walls 14. Porous walls 14 have a porosity designed to pass the gaseous constituents of diesel exhaust 50 and trap diesel particulates 52. Thus, diesel particulates 52 accumulate on and in walls 14, while the "cleaned" or "filtered" diesel exhaust 50' that passes through the walls exits DPF 10 through the adjacent channel 20 at (open) end 18.

This accumulation of diesel particulates 52 in DPF 10 ultimately reduces the performance of the engine in which the DPF resides, and reduces the DPF's durability. There is typically a threshold value $T_{DP}$ of the amount of diesel particulates $A_{DP}$ beyond which DPF 10 needs either to be replaced or "regenerated." The regeneration process involves heating DPF 10 to burn off the accumulated diesel particulates 52. However, to carry out DPF replacement or to initiate the regeneration process, it is necessary to have an accurate measure of the amount $A_{DP}$ of diesel particulates accumulated. An accurate measure of the amount $A_{DP}$ of accumulated diesel particulates also allows for an appropriate amount of heat to be used in the regeneration process, which is important because overheating can damage the DPF.

THz Characterization and Measurement Methods

An aspect of the present invention uses THz radiation to characterize and measure the amount $A_{DP}$ of diesel particulates accumulated in DPF 10. In an example embodiment, time-domain spectroscopy, or "THz-TDS" is employed. THz-TDS is a method by which femtosecond optical laser pulses generate broadband electromagnetic transient radiation. The temporal profile of the transient electromagnetic field associated with the electromagnetic transient radiation is a single-cycle oscillation with a full duration of ~1 psec ($1 \times 10^{-12}$ sec), while the spectral characteristics consist of frequency components that typically extend from 0.1 THz (100 GHz) to 10 THz or several 10s of THz.

Table 1 below shows the THz frequency range typically used in THz-TDS along with different units of measure, where f is frequency, $\lambda$ is wavelength, T is temperature and K is degrees Kelvin.

TABLE 1

Select THz frequencies in different units of measure

| f (THz) | $\lambda(\mu m)$ | Wavenumber (cm$^{-1}$) | Photon energy (meV) | T(K) |
|---|---|---|---|---|
| 0.2 | 1500 | 6.67 | 0.83 | 9.6 |
| 0.5 | 600 | 16.67 | 2.08 | 24.1 |
| 1 | 300 | 33.33 | 4.15 | 48.2 |
| 3 | 100 | 100.00 | 12.46 | 144.6 |
| 10 | 30 | 333.33 | 41.53 | 482.0 |

Example THz-TDS systems are described in U.S. Pat. No. 5,710,430 and Pre-Grant Published U.S. Patent Application No. 2008/0137068, which patent and which patent application are incorporated by reference herein. A suitable THz-TDS system adaptable for use in carrying out the methods of the present invention is the T-Ray 4000™ system available from Picometrix Inc., of Ann Arbor, Mich.

THz Measurement System

Figure 5:
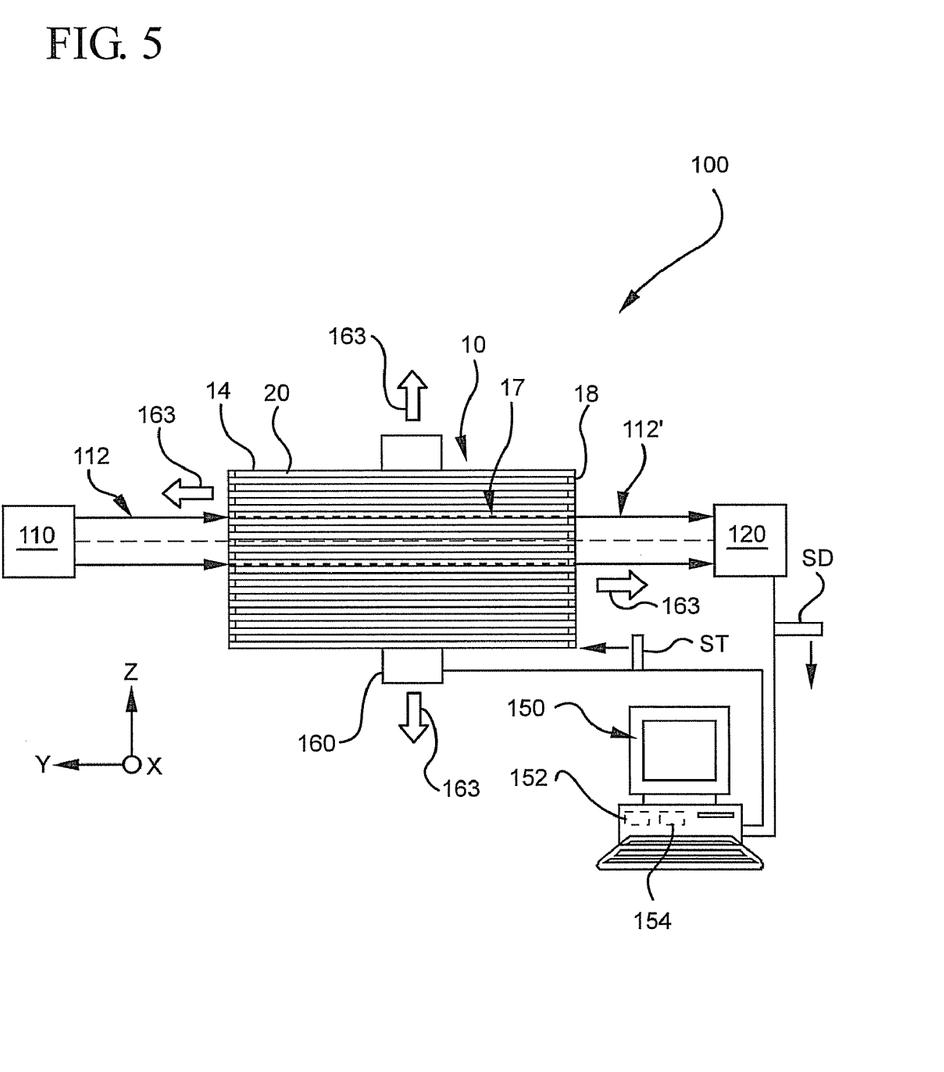
FIG. 5 is a schematic diagram of a generalized terahertz system with a DPF arranged therein.

FIG. 5 is a schematic diagram of a generalized terahertz (THz) measurement system ("THz system") 100 with a DPF 10 arranged therein. THz system 100 includes a THz-radiation emitter 110 that emits a beam 112 of THz-wavelength radiation along an axis A2. An example THz system 100 is a THz-TDS system, such as discussed above.

THz system 100 also includes a photodetector 120 arranged along axis A2 and configured to receive and detect THz-wavelength radiation in beam 112. DPF 10 is arranged along axis A2 between emitter 110 and detector 120, with its axis A1 substantially parallel to axis A2 so that THz radiation beam 112 passes longitudinally through DPF 10.

THz system 100 further includes a computer 150 electrically connected to detector 120. Computer 150 is, for example, a personal computer or other type of computer that includes a processor 152 and a computer-readable medium 154 (e.g., a memory unit) and that is capable of storing computer-readable instructions (e.g., software) and performing data acquisition and processing operations (e.g., data analysis) as discussed below. In an example embodiment, computer 150 includes data acquisition and processing software, such as LABVIEW from National Instruments, Inc. of Austin, Tex. In an example embodiment, computer 150 includes graphing, data analysis and image-processing software, such as the IGOR PRO 5 programming software tool available from Wavemetrics, Inc. of Oregon.

THz system 100 further includes an X-Y-Z translation stage 160 electrically connected to computer 150 and adapted to support DPF 10 and translate it relative to emitter 110 in response to a control signal ST from the computer. Translation in the Y and Z directions is indicated by arrows 163, while translation in the X directions is not shown. This arrangement allows for selecting a particular axial portion 17 of DPF 10 through which beam 112 can be made to pass.

In the operation of THz system 100 to measure a diesel particulate amount $A_{DP}$ in DPF 10, computer 150 directs translation stage 160 via control signal ST to set DPF 10 in a select position relative to axis A2. Beam 112 then passes longitudinally through axial portion 17 of DPF 10, and the transmitted beam 112' is detected by detector 120. In an example embodiment, this process is repeated for different axial portions 17 until substantially the entire DPF 10 is sampled. In another example embodiment, a single axial portion 17 includes all or substantially all of cells 20, so that all or substantially all of DPF 10 is covered in a single measurement.

In an example embodiment wherein diesel particulates 52 are substantially uniformly distributed through at least a portion of DPF 10, only one axial portion 17 is measured. Thus, in the methods of the present invention, at least one axial portion 17 of DPF 10 is measured. Detector 120 detects the THz electric field amplitude profile $E_{THz}(t)$ in transmitted beam 112' and in response thereto generates a detector signal SD representative of $E_{THz}(t)$. Detector signal SD is received and processed by computer 150. More specifically, the acquired data as provided to computer 150 by detector signals SD are analyzed by uploading the raw (measured) $E_{THz}(t)$ data (e.g., from memory unit 154 to processor 152) and performing a fast Fourier transform (FFT) to obtain the complex THz transmission spectrum ("spectrum") P(f), i.e., by performing the operation:

$$P(f)=FFT\{E_{THz}(t)\}.$$

In an example embodiment, a baseline spectrum $P_B(f)$ is acquired and is used as a differential reference of the THz transmission spectrum of the particular DPF 10 being measured. In an example embodiment, the baseline spectrum $P_B(f)$ is obtained by measuring an unloaded or substantially unloaded DPF 10 of the same DPF family as that being measured.

DPF Characterization and Measurement

The process of measuring the diesel particulate amount $A_{DP}$ in DPF 10 involves characterizing calibration spectra $P_C(f)$ for a given family of DPFs 10 for different diesel particulate amounts $A_{DP}$, and then performing a partial least squares (PLS) analysis on the spectra to establish a calibration relationship between the calibration spectra and the different diesel particulate amounts $A_{DP}$. In an example embodiment, a DPF "family" means DPFs having substantially the same length (or more generally, substantially the same dimensions), and substantially the same air-fill fraction, with the later generally defined by the thickness of walls 14 and the size and shape of cells 20. In an example embodiment, a DPF "family" further requires that the DPFs be formed from a common batch of ceramic-based material.

In an example embodiment, a single DPF 10 can be used to establish the calibration spectra $P_C(f)$. This involves loading the single DPF 10 with different select (i.e., known) amounts $A_{DP}$ of diesel particulates 52 and taking THz measurements for each select amount. In another example embodiment, different DPFs 10 in the same DPF family having different diesel particulate amounts $A_{DP}$ are used as the calibration samples. In an example embodiment, this includes a calibration sample that has substantially no diesel particulates.

An example characterization process was conducted using a single, square cross-sectioned DPF 10 having dimensions 2.5×2.5×3.5 cm. This DPF 10 was accurately weighed and its volume calculated, ignoring the small volume occupied by thin walls 14. A THz measurement was made in the manner discussed above for the "soot-free" DPF and the baseline spectrum $P_B(f)$ established. A known amount of "soot" 52 was then added to DPF 10. Degussa's Carbon black powder (Printex U) was used as a substitute for diesel-generated carbonized particulates. The soot 52 was distributed as evenly as possible in DPF 10. A THz measurement of the loaded DPF 10 was then taken and the time-domain data Fourier transformed to obtain the corresponding frequency domain spectra. The frequency domain spectra were further processed to yield a calibration spectrum $P_{C1}(f)$. This process was carried out using eleven different values for $A_{DP}$ in the single DPF. The $A_{DP}$ was adjusted in 1 g/L increments from 1 g/L to 12 g/L (11 g/L was omitted) to obtain calibration spectra $P_{Ci}(f)$ for i=1 to 11. In one example embodiment, the number N of "calibration samples" of DPFs 10 having known diesel particulate amounts $A_{DP}$ is in the range from 10 to 100, while in another example embodiment is in the range from 10 to 20.

In the experiments, a frequency bandwidth $B_f$ extending from about 0.2 THz to about 2.7 THz was used. It is noted here that while the use of a relatively wide bandwidth $B_f$ is generally advantageous, it is not required. In example embodiments, the frequency bandwidth $B_f$ consists of either the entire bandwidth $B_f$, or a narrower, discrete frequency range (including a single frequency) that allows for greater measurement sensitivity. For ease of integration of the invention into field applications (e.g., a garage, for example), the characterization and measurement methods can benefit from using a narrower, discrete frequency range, or a single frequency.

Thus, in an example embodiment, the calibration complex terahertz transmission spectra are measured over a frequency bandwidth $B_f$ that includes one or more frequencies in the frequency range 0.2 THz$\leq B_f \leq$2.7 THz. In a more general example embodiment, bandwidth $B_f$ includes one or more frequencies in a 2.5 THz band within a portion of the THz electromagnetic spectrum that ranges from 0.1 THz to 10 THz.

Figure 6:
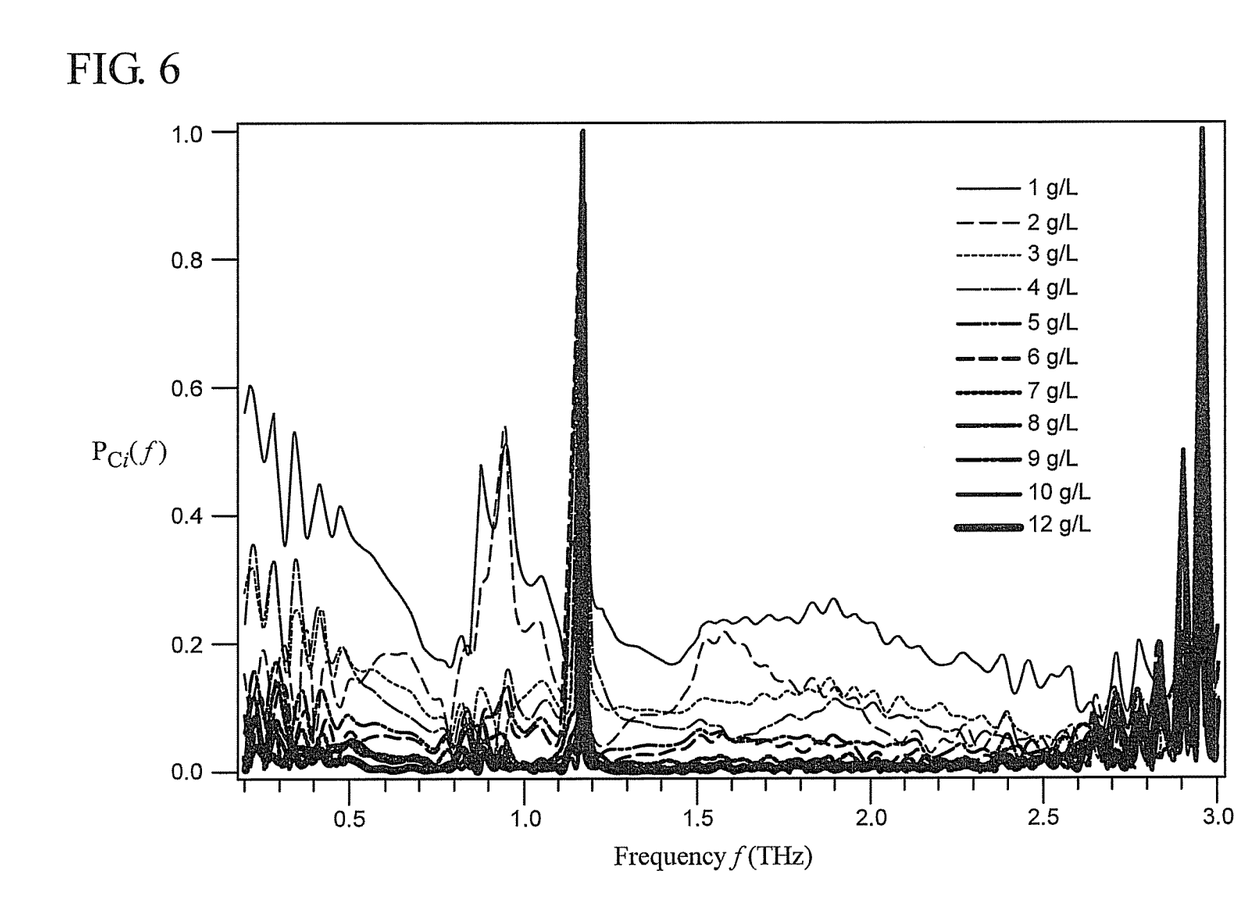
FIG. 6 plots eleven calibration complex terahertz transmission spectra $P_{Ci}(f)$ for eleven different diesel particulate amounts, wherein the calibration spectra are normalized to a baseline calibration spectrum obtained on a DPF having no diesel particulates.

FIG. 6 plots the eleven calibration spectra $P_{Ci}(f)$ as normalized to the baseline spectrum $P_B(f)$ for the eleven different values of $A_{DP}$. The plot of FIG. 6 shows that the THz transmission through DPF 10 decreases as the diesel particulate accumulation level increases. These data were then subjected to a partial least squares (PLS) analysis to establish a correlation between the predicted vs. actual diesel particulate amounts $A_{DP}$.

Figure 7:
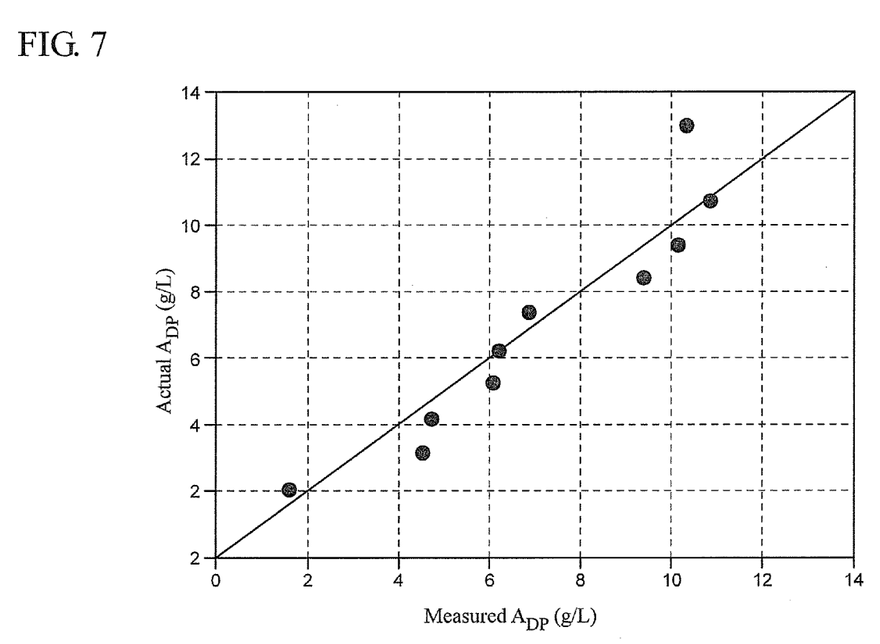
FIG. 7 plots the actual amounts of diesel particulates (g/L) added to the DPF for calibration purposes (Y axis) versus the measured amounts of diesel (X-axis) as determined by a partial least squares analysis that takes into account values of the calibration spectra over substantially the entire frequency bandwidth.
Figure 8:
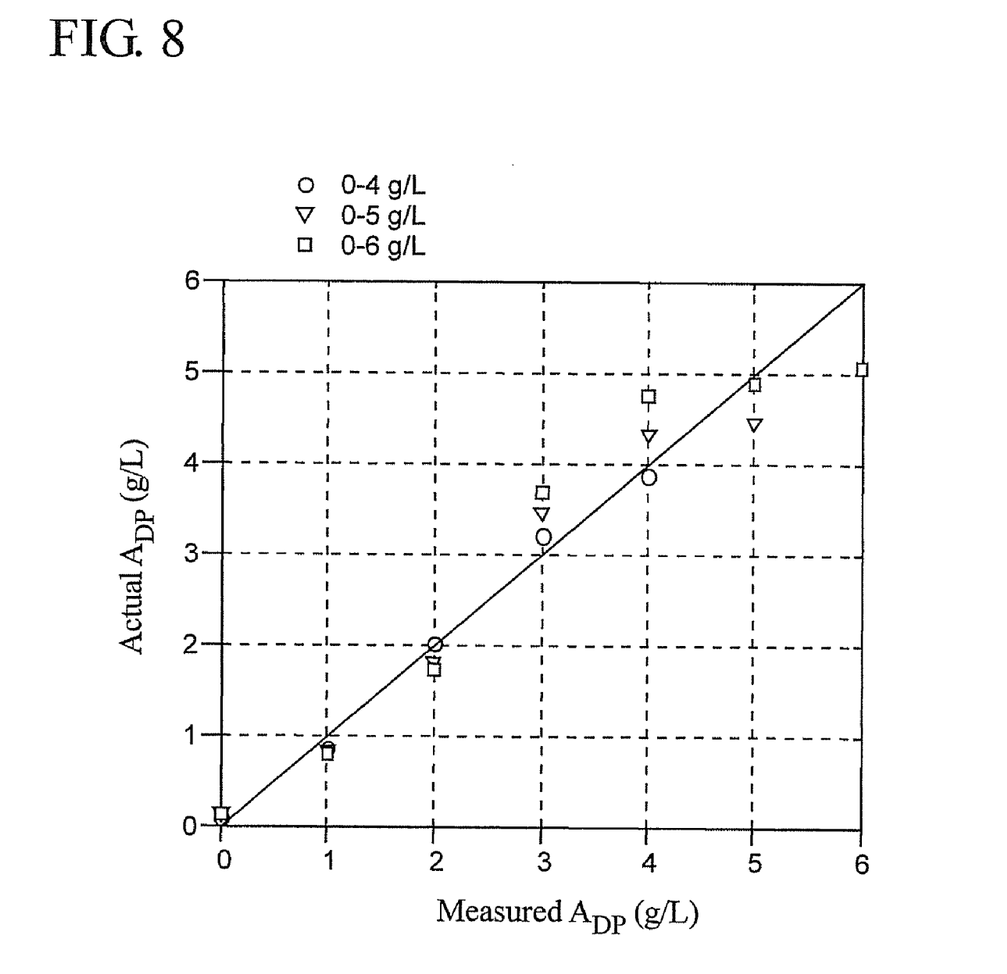
FIG. 8 is similar to FIG. 7, except that microwave-wavelength radiation was used instead of terahertz-wavelength radiation, with the plot of FIG. 8 showing a limited correlation range for the diesel particulate amount as compared to that of FIG. 7.

FIG. 7 plots the measured vs. actual diesel particulate amounts $A_{DP}$ (g/L) as determined by the PLS analysis. The plot shows a very strong correlation between measured and actual diesel particulate amounts $A_{DP}$ all the way up to about 11 g/L. As a comparison, a similar plot of the correlation between measured and actual diesel particulate amounts $A_{DP}$ using microwave techniques is shown in FIG. 8. The correlation in FIG. 8 deviates from linearity above 5 g/L.

Based on experimental evidence, the inventors believe that the THz measurement methods of the present invention are suitable for establishing a calibration relationship, such as a linear dependence, for the measured vs. actual diesel particulate amounts $A_{DP}$ in a range 0 g/L$\leq A_{DP} \leq$20 g/L, where the diesel particulate accumulation is anticipated to be correspondingly large, as well for a more limited range 0 g/L$\leq A_{DP} \leq$12 g/L for those applications where the diesel particulate accumulation is anticipated to be correspondingly limited. When referring to particulate filters PF generally (as for use on gasoline, natural gas or diesel fueled engines, or other uses as described herein), the particulate amount is represented by the term $A_P$ instead of $A_{DP}$ as would be the case when referring specifically to diesel particulate filters. For filters specific to gasoline and natural gas fuel engines the term corresponding to $A_{DP}$ would be $A_{GP}$ or $A_{NP}$, respectively.

The PLS analysis uses principal component analysis (PCA) to construct the latent variable space by maximizing the covariance of X and Y, where X is the measured calibration spectra $P_{Ci}(f)$ and Y=$A_{DP}$. In an example embodiment, computer 150 includes software that performs the PLS analysis. Example software for performing the PLS analysis is, for example, the MATLAB-based PLS toolbox software, available from The Mathworks, Inc. of Natick, Mass. Unlike the traditional univariate (i.e., single-point) data analysis approach in which a single value associated with a frequency shift or an amplitude change is used to relate to the diesel particulate amount $A_{DP}$, the PLS approach of the present invention uses a multivariate approach. The multivariate PLS approach uses substantially all of the magnitude information in the entire THz frequency range (i.e., bandwidth $B_f$) to build a linear model in a lower dimensional space. This PLS approach accurately predicts the diesel particulate amount $A_{DP}$ and can be used to validate measurement device calibration and experiment set up from data repeatability analysis.

Once the correlation between actual and measured diesel particulate amounts $A_{DP}$ is established for a particular family of DPFs, then, in an example embodiment, THz system 100 is used to measure a subject DPF 10 for which the diesel particulate amount $A_{DP}$ is unknown. This process involves calculating the subject spectrum $P_S(f)$ for the subject DPF 10 having the unknown diesel particulate content and comparing it to the correlation data, such as plotted in FIG. 7, to yield a measured value for the diesel particulate amount $A_{DP}$.

In an example embodiment, the methods of the present disclosure include regenerating the subject DPF 10 if the measured diesel particulate amount $A_{DP}$ exceeds a particulate accumulation threshold value $T_{DP}$.

In an additional embodiment the disclosure is directed to a method of characterizing particulate accumulation in a family of particulate filters having a longitudinal axis and opposite first and second ends connected by an array of cells generally directed along the longitudinal axis; measuring a calibration complex terahertz transmission spectra of at least a portion of at least one filter in the particulate filter family and having different known particulate amounts $A_{DP}$; and performing a partial least squares (PLS) analysis on the calibration complex terahertz transmission spectra, thereby establishing a linear calibration relationship between the calibration complex terahertz transmission spectra and the particulate amounts $A_{DP}$. The filter can be selected from the group consisting of a filter suitable for removing particulates from a fluid and a filter suitable for concentrating a particulate in a fluid while simultaneously allow for the passage of a fluid free of particulates or substantially free of particulates to pass through the interior walls of said filter; said particulate is selected from the group consisting of a chemical, biological and inorganic particulate, and a carbonaceous particulate resulting from the combustion of a hydrocarbon fuel.

In a further embodiment the disclosure is directed to a method of characterizing an article of manufacture to determine a specified property of said article, said article having a longitudinal axis and opposite first and second ends connected by an array of cells generally directed along the longitudinal axis, said method comprising measuring a complex terahertz transmission spectra of at least a portion of at least one article in a family of said articles; performing a partial least squares (PLS) analysis on the complex terahertz transmission spectrum said article; and comparing the transmission spectrum of said article with a calibration spectrum for the specified property to thereby determine whether said article has or does not have the specified property. The property to be measured is selected from the group consisting of water remaining in the article after the article has been heat treated to a selected temperature for a selected time, thickness of the cells walls of said article, the presence of cracks in the walls of said article In a further embodiment, the invention is directed to a method of characterizing particulate accumulation in particulate filters (PFs). The particulates (or soot) can be from diesel, gasoline and natural gas fueled engines, fluid streams bearing dust, and chemical and biological substances such as may be found in laboratory fluids, for example, air. The PFs are characterized as having a longitudinal axis and opposite first and second ends connected by an array of cells generally directed along the longitudinal axis, comprising measuring calibration complex terahertz transmission spectra of at least a portion of at least one PF in the PF family and having different known particulate amounts $A_P$; and performing a partial least squares (PLS) analysis on the calibration complex terahertz transmission spectra, thereby establishing a calibration relationship between the calibration complex terahertz transmission spectra and the diesel particulate amounts $A_P$. In one aspect, the method comprises measuring the calibration complex terahertz transmission spectra for between 10 and 100 different known particulate amounts A. The method further comprises measuring the calibration complex terahertz transmission spectra for between 10 and 20 different known particulate amounts A. The method further comprises providing a single PF with the different known diesel particulate amounts $A_P$; and measuring one of the calibration complex terahertz transmission spectra for each of the different diesel particulate amounts A. Additionally, measuring the calibration complex terahertz transmission spectra further comprises passing terahertz radiation longitudinally between the first and second ends of the at least one PF and detecting the terahertz radiation adjacent the second end. The terahertz radiation through substantially all of the cells of the at least one PF. The calibration relationship has a particulate amount $A_P$ in the range $0\ g/L \leq A_P \leq 20\ g/L$. The method additionally comprises measuring a complex terahertz transmission spectrum for a subject PF in the family of PFs and having an unknown amount of particulate accumulation; and comparing the subject complex terahertz transmission spectrum to the calibration relationship, thereby establishing a measured amount of particulate accumulation for the subject PF. The subject PF can be from a diesel, gasoline or natural gas fueled engines;, fluid streams bearing dust or particulate matter, and chemical and biological substances such as may be found in laboratory fluids, for example, air.

It will be apparent to those skilled in the art that various modifications to the example embodiments of the disclosure as described herein can be made without departing from the spirit or scope of the invention as defined in the appended claims. Thus, it is intended that the present invention covers the modifications and variations of this disclosure provided they come within the scope of the appended claims and the equivalents thereto.

What is claimed is:

1. A method of characterizing particulate accumulation in a family of particulate filters (PFs) having a longitudinal axis and opposite first and second ends connected by an array of cells generally directed along the longitudinal axis, comprising:

measuring calibration complex terahertz transmission spectra of at least a portion of at least one PF in the PF family and having different known 1 particulate amounts $A_P$; and performing a partial least squares (PLS) analysis on the calibration complex terahertz transmission spectra, thereby establishing a calibration relationship between the calibration complex terahertz transmission spectra and the particulate amounts $A_P$.

2. The method of claim 1, further comprising:
measuring the calibration complex terahertz transmission spectra for between 10 and 100 different known particulate amounts $A_P$.

3. The method of claim 2, further comprising:
measuring the calibration complex terahertz transmission spectra for between 10 and 20 different known particulate amounts $A_P$.

4. The method of claim 1, further comprising:
providing a single PF with the different known particulate amounts $A_P$; and
measuring one of the calibration complex terahertz transmission spectra for each of the different particulate amounts $A_P$.

5. The method of claim 1, wherein measuring the calibration complex terahertz transmission spectra further comprises:
passing terahertz radiation longitudinally between the first and second ends of the at least one PF and detecting the terahertz radiation adjacent the second end.

6. The method of claim 5, further comprising: passing the terahertz radiation through substantially all of the cells of the at least one PF.

7. The method of claim 1, wherein the calibration relationship has a particulate amount $A_P$ in the range $0 \text{ g/L} \leq A_P \leq 20$ g/L.

8. The method of claim 1, wherein the PFs in the family of PFs each have an air-fill fraction that is substantially the same and a length that is substantially the same.

9. The method of claim 1, further comprising:
measuring a complex terahertz transmission spectrum for a subject PF in the family of PFs and having an unknown amount of particulate accumulation; and
comparing the subject complex terahertz transmission spectrum to the calibration relationship, thereby establishing a measured amount of particulate accumulation for the subject PF.

10. The method of claim 9, further comprising obtaining the subject PF from an engine selected from the group consisting of diesel, gasoline and natural gas fueled engines.

11. A method of measuring an amount of accumulated diesel particulates in a subject diesel particle filter (DPF) of a family of DPFs characterized by a longitudinal axis and opposite first and second ends connected by an array of cells generally directed along the longitudinal axis, the method comprising:
obtaining a DPF from a diesel engine;
passing terahertz radiation through at least a portion of the array of cells from the first to the second end of the subject DPF to form transmitted terahertz radiation;
detecting the transmitted terahertz radiation;
forming a subject complex terahertz transmission spectrum from the detected transmitted terahertz radiation; and
comparing the subject complex terahertz transmission spectrum to a calibration relationship established by performing a partial least squares analysis on calibrated complex terahertz transmission spectra of at least one calibration DPF in the DPF family and having different known amounts of diesel particulates.

12. The method of claim 11, further comprising:
providing between 10 and 100 known different diesel particulate amounts $A_{DP}$ for the at least one calibration DPF.

13. The method of claim 11, further comprising:
regenerating the subject DPF if the measured diesel particulate amount exceeds a particulate accumulation threshold value.

14. The method of claim 11, further comprising:
providing one of the at least one calibration DPF in the DPF family to have substantially no particulate accumulation.

15. The method of claim 11, further comprising:
passing the terahertz radiation through substantially the entire array of cells of the subject DPF.

16. A method of establishing a measured amount of diesel particulate accumulation in a subject diesel particulate filter (DPF) of a family of DPFs characterized by a longitudinal axis and opposite first and second ends connected by an array of cells generally directed along the longitudinal axis, comprising:
measuring calibration complex terahertz transmission spectra of at least a portion of at least one DPF in the DPF family and having different known amounts of diesel particulates;
performing a partial least squares (PLS) analysis on the calibration complex terahertz transmission spectra, thereby establishing a calibration relationship between the calibration complex transmission spectra and amounts of diesel particulates;
measuring a subject complex terahertz transmission spectrum for the subject DPF;
comparing the subject complex terahertz transmission spectrum to the calibration relationship to establish a measured amount of diesel particulates in the subject DPF.

17. The method of claim 16, wherein the family of DPFs is constituted by the DPFs having an air-fill fraction that is substantially the same, and a length that is substantially the same.

18. The method of claim 16, further comprising:
measuring the select calibration complex terahertz transmission spectra and the subject complex transmission spectra using terahertz time-domain spectroscopy.

19. The method of claim 16, wherein the calibration complex terahertz transmission spectra are measured over a frequency bandwidth $B_f$ that includes one or more frequencies in a 2.5 THz wide band between 0.1 THz and 10 THz.

20. A method of characterizing particulate accumulation in a family of particulate filters having a longitudinal axis and opposite first and second ends connected by an array of cells generally directed along the longitudinal axis, comprising:
measuring calibration complex terahertz transmission spectra of at least a portion of at least one filter in the particulate filter family and having different known particulate amounts $A_{DP}$; and
performing a partial least squares (PLS) analysis on the calibration complex terahertz transmission spectra, thereby establishing a calibration relationship between the calibration complex terahertz transmission spectra and the particulate amounts $A_{DP}$.

21. The method according to claim 20, wherein:
said filter is selected from the group consisting of a filter suitable for removing particulates from a fluid and a filter suitable for concentrating a particulate in a fluid while simultaneously allow for the passage of a fluid free of particulates or substantially free of particulates to pass through the interior walls of said filter;
said particulate is selected from the group consisting of a chemical, biological and inorganic particulate, and a carbonaceous particulate resulting from the combustion of a hydrocarbon fuel.

* * * * *